US00PP33648P2

(12) United States Plant Patent
van Sambeek

(10) Patent No.: US PP33,648 P2
(45) Date of Patent: Nov. 16, 2021

(54) *LAVANDULA* PLANT NAMED 'DOLAVIMP'

(50) Latin Name: *Lavandula dentata*
Varietal Denomination: Dolavimp

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/139,924

(22) Filed: Dec. 31, 2020

(51) Int. Cl.
*A01H 6/50* (2018.01)
*A01H 5/02* (2018.01)

(52) U.S. Cl.
USPC ..... Plt./417

(58) Field of Classification Search
USPC ..... Plt./417
See application file for complete search history.

(56) References Cited

PUBLICATIONS

PLUTO Plant Variety Database Apr. 17, 2021.*

* cited by examiner

*Primary Examiner* — Annette H Para
(74) *Attorney, Agent, or Firm* — C. Anne Whealy

(57) ABSTRACT

A new and distinct cultivar of *Lavandula* plant named 'Dolavimp', characterized by its upright plant habit and medium plant height; freely branching growth habit; early and freely flowering habit; dark violet-colored flowers positioned on strong peduncles; and good garden performance.

1 Drawing Sheet

Botanical designation: *Lavandula dentata.*
Cultivar denomination: 'DOLAVIMP'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Aug. 24, 2020, application number 2020/1985. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct *Lavandula* plant, botanically known as *Lavandula dentata*, commonly referred to as Lavender and hereinafter referred to by the name 'Dolavimp'.

The new *Lavandula* plant is a product of a planned breeding program conducted by the Inventor in De Lier, The Netherlands. The objective of the breeding program was to develop new unique *Lavandula* plants with long flowering period and attractive plant form and flower coloration.

The new *Lavandula* plant originated from an open-pollination in April, 2015 of an unnamed proprietary selection of *Lavandula dentata*, not patented, as the female, or seed, parent with an unknown selection of *Lavandula dentata* as the male, or pollen, parent. The new *Lavandula* plant was discovered and selected by the Inventor as a single flowering plant within the progeny of the stated open-pollination in a controlled environment in De Lier, The Netherlands in April, 2016.

Asexual reproduction of the new *Lavandula* plant by terminal cuttings in a controlled greenhouse environment in De Lier, The Netherlands since June, 2016 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Dolavimp' as a new and distinct *Lavandula* plant:

1. Upright plant habit and medium plant height.
2. Freely branching growth habit.
3 Early and freely flowering habit.
4. Dark violet-colored flowers positioned on strong peduncles.
5. Good garden performance.

Plants of the new *Lavandula* differ primarily from plants of the female parent selection primarily in plant habit as plants of the new *Lavandula* are more uniform than plants of the female parent selection.

Plants of the new *Lavandula* can be compared to plants of the *Lavandula dentata* 'Royal Crown', not patented. In side-by-side comparisons, plants of the new *Lavandula* differ primarily from plants of 'Royal Crown' in plant size as plants of the new *Lavandula* are more compact than and not as tall as plants of 'Royal Crown'.

BRIEF DESCRIPTION OF THE PHOTOGRAPH

The accompanying photograph illustrates the overall appearance of the new *Lavandula* plant showing the colors as true as it is reasonably possible to obtain in colored reproductions of this type. Colors in the photograph may differ slightly from the color values cited in the detailed botanical description which accurately describe the colors of the new *Lavandula* plant.

The photograph is a side perspective view of a typical flowering plant of 'Dolavimp' grown in a container.

DETAILED BOTANICAL DESCRIPTION

The aforementioned photograph and following observations and measurements describe plants grown in 17-cm containers in Aalsmeer, The Netherlands during the summer initially in a greenhouse and finished in an outdoor nursery and under conditions and cultural practices which approximate those generally used in commercial *Lavandula* plant production. During the production of the plants, day temperatures averaged 21° C. and night temperatures averaged 15° C. Plants were 23 weeks old when the photographs and description were taken. In the following description, color references are made to The Royal Horticultural Society Colour Chart, Second Edition, except where general terms of ordinary dictionary significance are used. Measurements represent averages for typical flowering plants.

Botanical classification: *Lavandula dentata* 'Dolavimp'.

Parentage:

*Female, or seed, parent*.—Unnamed proprietary selection of *Lavandula dentata*, not patented.

*Male, or pollen, parent*.—Unknown selection of *Lavandula dentata*, not patented.

Propagation:

*Type*.—Terminal vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Medium in thickness, fibrous; typically white to light yellow in color, actual color of the roots is dependent on substrate composition, water quality, fertilizer type and formulation.

*Rooting habit*.—Moderately freely branching; medium density.

Plant description:

*Plant and growth habit*.—Herbaceous perennial; upright plant habit; broadly obovate in overall plant shape; freely branching habit; moderately vigorous growth habit; moderate growth rate; flowers arranged in verticillasters on crowded spikes with showy terminal flower bracts.

*Plant height, soil level to top of floral plane*.—About 44 cm.

*Plant width*.—About 28 cm.

*Lateral branch description*.—Quantity per plant: Freely branching with about four primary lateral branches each with about 18 secondary lateral branches developing per plant. Length: About 14 cm. Diameter: About 9 mm. Internode length: About 1.7 cm. Strength: Strong. Aspect: About 20° to 40° from vertical. Texture and luster: Densely pubescent; semi-glossy. Color, when developing: Close to 143A. Color, developed: Close to 199D.

*Leaf description*.—Arrangement: Opposite and decussate, simple; sessile. Length: About 4 cm. Width: About 1 cm. Shape: Lanceolate. Apex: Acute. Base: Truncate. Margin: Crenate with deep parallel lobes. Texture and luster, upper surface: Pubescent; semi-glossy. Texture and luster, lower surface: Pubescent; matte. Fragrance: Strongly aromatic, pungent. Venation pattern: Pinnate. Color: Developing leaves, upper surface: Close to 137A. Developing leaves, lower surface: Close to 138C. Fully expanded leaves, upper surface: Close to 137A; venation, close to 137A. Fully expanded leaves, lower surface: Close to 138B; venation, close to 138B.

Flower description:

*Flower type, arrangement and habit*.—Single bilabiate flowers arranged in compact verticillasters on crowded terminal spikes; freely flowering, about 86 to 122 flowers developing per inflorescence and about 4,050 flowers developing per plant; flowers with two-lobed upper lip and three-lobed lower lip; flowers face mostly outwardly on the spike; inflorescences with showy terminal flower bracts.

*Natural flowering season*.—Flowering is continuous from June to August in The Netherlands; plants begin flowering about eleven weeks after planting.

*Flower longevity on the plant*.—Inflorescences last about three to four weeks on the plant; flowers persistent.

*Fragrance*.—Strongly fragrant; typical lavender scent.

*Flower buds*.—Length: About 7 mm. Diameter: About 3 mm. Shape: Elliptic. Texture and luster: Pubescent; matte. Color: Close to 144B.

*Inflorescence size*.—Length: About 4 cm to 7 cm. Diameter: About 1 cm to 1.5 cm.

*Flower size*.—Diameter: About 3 mm by 4 mm. Depth (height): About 5 mm. Throat diameter: About 1.5 mm. Tube length: About 6 mm. Tube diameter: About 1 mm.

*Petals*.—Quantity and arrangement: Upper lip, two-lobed and lower lip, three-lobed. Length: About 2 mm. Width: About 1 mm. Shape: Lanceolate; proximally, fused into a tube. Apex: Obtuse, rounded. Margin: Entire; not undulate. Texture and luster, upper surface: Smooth, glabrous; matte. Texture and luster, lower surface: Pubescent; matte. Texture, throat and tube: Pubescent; matte. Color: When opening and fully opened, upper surface: Close to 92A; venation, close to 92A; color becoming closer to 91A with development. When opening and fully opened, lower surface: Close to 92A; venation, close to 92A; color does not change with development.

Throat: Close to 155D; venation, close to 155D. Tube: Close to 155D; venation, close to 155D.

*Terminal flower bracts*.—Quantity and arrangement: About four positioned at inflorescence apex. Length: About 1 cm. Width: About 8 mm. Shape: Rhomboidal. Apex: Acute. Margin: Entire. Texture and luster, upper and lower surfaces: Pubescent; matte. Color, upper and lower surfaces: Close to 88A.

*Basal flower bracts*.—Quantity and arrangement: Subtending the flowers is a single basal flower bract. Length: About 8 mm. Width: About 1 cm. Shape: Cordate. Apex: Emarginate. Base: Cuneate. Margin: Entire. Texture, upper and lower surfaces: Pubescent. Color, upper and lower surfaces: Close to 187B with 141A and 155D.

*Sepals*.—Quantity and arrangement: Five, fused forming an urceolate calyx. Length: About 6 mm. Width: About 2 mm. Shape: Subulate. Apex: Acuminate. Margin: Entire. Texture and luster, upper surface: Pubescent; matte. Texture and luster, lower surface: Smooth, glabrous; glossy. Color: When opening, upper and lower surfaces: Close to 143A. Fully opened, upper and lower surfaces: Close to 143A.

*Peduncles*.—Length: About 23 cm. Diameter: About 3 mm. Aspect: Upright to about 30° from vertical. Strength: Strong to moderately strong. Texture and luster: Pubescent; semi-glossy. Color: Close to 137A.

*Pedicels*.—Length: About 2 mm. Diameter: About 1 mm. Aspect: About 30° from peduncle axis. Strength: Moderately strong. Texture and luster: Pubescent; semi-glossy. Color: Close to 142A.

*Reproductive organs*.—Stamens: Quantity per flower: Four. Filament length: About 1 mm. Filament color: Close to 155D. Anther shape: Reniform; dorsifixed. Anther size: About 1 mm by 0.5 mm. Anther color: Close to 79A and 17A. Pollen amount: Abundant. Pollen color: Close to 14A. Pistils: Quantity per flower: One. Pistil length: About 4 mm. Stigma shape: Capitate. Stigma diameter: About 0.5 mm. Stigma color: Close to 202A. Style length: About 3 mm. Style color: Close to 145D. Ovary color: Close to 145B.

*Seeds and fruits*.—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain, wind and to tolerate temperatures ranging from −15° C. to about 35° C. and to be suitable for USDA Hardiness Zone 7.

It is claimed:

1. A new and distinct *Lavandula* plant named 'Dolavimp' as illustrated and described.

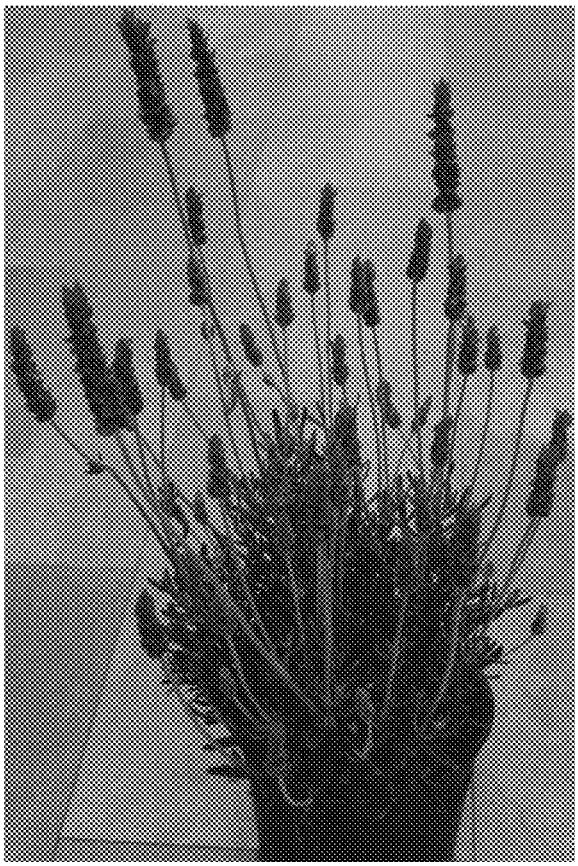

* * * * *